United States Patent
Cohen

(10) Patent No.: US 7,019,010 B2
(45) Date of Patent: *Mar. 28, 2006

(54) COMBINATIONS

(75) Inventor: David Saul Cohen, New Providence, NJ (US)

(73) Assignee: Novertis AG, Basel (CH)

( * ) Notice: Subject to any disclaimer, the term of this patent is extended or adjusted under 35 U.S.C. 154(b) by 145 days.

This patent is subject to a terminal disclaimer.

(21) Appl. No.: 10/236,651

(22) Filed: Sep. 6, 2002

(65) Prior Publication Data

US 2003/0139429 A1 Jul. 24, 2003

Related U.S. Application Data

(63) Continuation-in-part of application No. 10/231,427, filed on Aug. 28, 2002, now abandoned.

(60) Provisional application No. 60/325,485, filed on Sep. 27, 2001.

(51) Int. Cl.
*A61K 31/522* (2006.01)

(52) U.S. Cl. ............................................. 514/263.34

(58) Field of Classification Search ................ 514/263, 514/263.34
See application file for complete search history.

(56) References Cited

U.S. PATENT DOCUMENTS 5,260,332 A * 11/1993 Dufresne .................... 514/452
2003/0171384 A1 * 9/2003 Bhalay et al. ......... 514/263.22

FOREIGN PATENT DOCUMENTS

| WO | WO 00/37061 | 6/2000 |
| WO | WO 2001/19357 A2 * | 3/2001 |
| WO | WO 02/13798 A2 | 2/2002 |
| WO | WO 03/099194 A2 | 4/2003 |
| WO | WO 2004002461 | 1/2004 |

OTHER PUBLICATIONS

Khan et al. 'Endothelin and erectile dysfunction: a target for pharmaceutical intervention,' Exp. Opin. Invest. Drugs, 1998, vol. 7 No. 11, pp. 1759-1767.*

* cited by examiner

*Primary Examiner*—Shengjun Wang
(74) *Attorney, Agent, or Firm*—Cynthia Zhang; Gregory D. Ferraro

(57) ABSTRACT

The present invention relates to a pharmaceutical composition, comprising
(a) a phosphodiesterase 5 inhibitor or a pharmaceutically acceptable salt thereof and
(b) at least one of the active ingredients selected from the group consisting of
  (i) an anti-diabetic agent;
  (ii) HMG-Co-A reductase inhibitors;
  (iii) an anti-hypertensive agent; and
  (iv) a serotonin reuptake inhibitor (SSRI)
or, in each case, or a pharmaceutically acceptable salt thereof and a pharmaceutically acceptable carrier. The pharmaceutical composition may be employed for the treatment of sexual dysfunction, hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, obesity, diabetic retinopathy, diabetic nephropathy, glomerulosclerosis, diabetic neuropathy, syndrome X, erectile dysfunction, coronary heart disease, hypertension, especially ISH, angina pectoris, myocardial infarction, stroke, vascular restenosis, endothelial dysfunction, impaired vascular compliance, congestive heart failure.

11 Claims, No Drawings

COMBINATIONS

COMBINATIONS

The present invention relates to a combination, especially a pharmaceutical composition, comprising
(a) a PDE 5 inhibitor or a pharmaceutically acceptable salt thereof and
(b) at least one active ingredient selected from the group consisting of
  (i) an anti-diabetic agent;
  (ii) HMG-Co-A reductase inhibitors;
  (iii) an anti-hypertensive agent; and
  (iv) a serotonin reuptake inhibitor (SSRI)
  or, in each case, a pharmaceutically acceptable salt thereof;

and a pharmaceutically acceptable carrier.

PDE5 inhibitors include compounds of formula

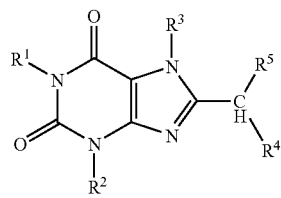

I in free or salt form, where
$R^1$ is hydrogen or alkyl optionally substituted by hydroxy, alkoxy, or alkylthio,
$R^2$ is hydrogen, alkyl, hydroxyalkyl, alkylcarbonyloxyalkyl, alkoxyalkyl, alkylthioalkyl, alkenyl, cycloalkylalkyl, heterocyclylalkyl, aralkyl in which the aryl ring thereof is optionally fused to a 5-membered heterocyclic group or is optionally substituted by one or more substituents selected from alkoxy, amino, alkylamino, dialkylamino, acylamino, halogen, hydroxy, aminosulfonyl, alkylaminosulfonyl, dialkylaminosulfonyl, alkylsulfonylamino or dialkylaminosulfonylamino,
$R^3$ is hydrogen or alkyl optionally substituted by hydroxy, alkoxy, or alkylthio,
$R^4$ is hydrogen or alkyl,
$R^5$ is a quinolinyl, isoquinolinyl or oxodihydroisoquinolinyl group optionally fused to a 5-membered heterocyclic group and optionally substituted by one or more substituents selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —N($R^6$)$R^7$, aryl optionally substituted by one or more substituents selected from halogen or alkoxy, or heteroaryl having 5 or 6 ring atoms, attached through a ring carbon atom to the indicated carbon atom, and
$R^6$ and $R^7$ are each independently hydrogen or alkyl optionally substituted by hydroxy or alkoxy or one of $R^6$ and $R^7$ is hydrogen and the other is acyl, or $R^6$ and $R^7$ together with the nitrogen atom to which they are attached denote a 5- or 6-membered heterocyclyl group.

"Alkyl" as used herein denotes straight chain or branched alkyl, which may be, for example, $C_1$–$C_{10}$-alkyl such as methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl or straight or branched decyl. Preferably alkyl is $C_1$–$C_8$-alkyl.

"Alkoxy" as used herein denotes straight chain or branched alkoxy which may be, for example, $C_1$–$C_{10}$-alkoxy such as methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, straight or branched octyloxy, straight or branched nonyloxy or straight or branched decyloxy. Preferably, alkoxy is $C_1$–$C_4$-alkoxy.

"Alkylthio" as used herein may be $C_1$ to $C_{10}$-alkylthio such as methylthio, ethylthio, n-propylthio, isopropylthio, n-butylthio, sec-butylthio, isobutylthio, tert-butylthio, pentylthio, hexylthio, heptylthio, octylthio, nonylthio or decylthio. Preferably alkylthio is $C_1$ to $C_4$-alkylthio.

"Alkenyl" as used herein means straight chain or branched alkenyl, which may be, for example, $C_2$ to $C_{10}$-alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$ to $C_4$-alkenyl.

"Cycloalkylalkyl" as used herein denotes alkyl, for example $C_1$ to $C_{10}$-alkyl such as one of the $C_1$ to $C_{10}$-alkyl groups hereinbefore mentioned, substituted by a $C_3$ to $C_8$ cycloalkyl group such as cyclopropyl, methylcyclopropyl, cyclobutyl, cyclopentyl, cyclohexyl, methylcyclohexyl, dimethylcyclohexyl, cycloheptyl or cyclooctyl. Preferably, cycloalkylalkyl is $C_3$–$C_6$-cycloalkyl-$C_1$–$C_4$-alkyl.

"Heterocyclylalkyl" as used herein denotes alkyl, for example $C_1$ to $C_{10}$-alkyl such as one of the $C_1$ to $C_{10}$-alkyl groups hereinbefore mentioned, substituted by a 5- or 6-membered heterocyclyl group having one or two hetero atoms selected from nitrogen, oxygen and sulfur in the ring, such as pyrrolyl, pyrrolidinyl, furyl, thienyl, pyridyl, piperidyl, imidazolyl, imidazolidinyl, pyrazolidinyl, piperazinyl, morpholinyl, oxazolyl, or furazanyl. Preferably, heterocyclylalkyl is $C_1$–$C_4$-alkyl substituted by a 5- or 6-membered heterocyclyl group having one or two nitrogen or oxygen atoms or one nitrogen atom and one oxygen atom in the ring.

"Aralkyl" as used herein means $C_6$–$C_{10}$-aryl-$C_1$–$C_{10}$ alkyl and may be, for example, one of the $C_1$–$C_{10}$-alkyl groups mentioned hereinbefore, particularly one of the $C_1$–$C_4$-alkyl groups, substituted by phenyl, tolyl, xylyl or naphthyl. Preferably, aralkyl is phenyl-$C_1$–$C_4$-alkyl, particularly benzyl or 2-phenylethyl.

"Acyl" as used herein denotes alkylcarbonyl, for example $C_1$–$C_{10}$-alkylcarbonyl where $C_1$–$C_{10}$-alkyl may be one of the $C_1$–$C_{10}$-alkyl groups hereinbefore mentioned, optionally substituted by one or more halogen atoms; cycloalkylcarbonyl, for example $C_3$–$C_8$-cycloalkylcarbonyl where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$–$C_{10}$-arylcarbonyl such as benzoyl; or aralkylcarbonyl, for example $C_6$ to $C_{10}$-aryl-$C_1$–$C_4$-alkylcarbonyl such as benzylcarbonyl or phenylethylcarbonyl. Preferably acyl is $C_1$–$C_4$-alkylcarbonyl.

"Alkynyl" as used herein denotes straight or branched alkynyl, for example $C_2$ to $C_6$-alkynyl such as ethynyl, propargyl, 2-butynyl, pentynyl or hexynyl. Preferably alkynyl is $C_2$–$C_4$-alkynyl.

"Aryl" as used herein denotes a monovalent carbocylic aromatic group, for example $C_6$–$C_{10}$-aryl such as phenyl, phenyl substituted by one or more, e.g. one, two or three, $C_1$–$C_4$-alkyl groups, or naphthyl. Preferably aryl is phenyl.

"Heteroaryl having 5 or 6 ring atoms" as used herein denotes a monovalent aromatic heterocyclic group having 5 or 6 ring atoms of which one, two or three are selected from nitrogen, oxygen and sulfur, such as pyrrolyl, furyl, thienyl, pyridyl, pyrazolyl, imidazolyl, triazolyl, oxazolyl, isoxazolyl, thiazolyl, isothiazolyl, dithiazolyl, trithiazolyl, furazanyl, pyrazinyl, pyrimidinyl or triazinyl.

In alkylamino, dialkylamino, acylamino, dialkylaminosulfonylamino, alkylcarbonyl, alkylcarbonyloxy, alkoxycarbonyl, hydroxyalkyl, alkylthioalkyl and alkoxyalkyl, the alkyl, acyl or alkoxy groups as appropriate have the meanings hereinbefore described.

"Halogen" as used herein may be fluorine, chlorine, bromine or iodine; preferably it is fluorine, chlorine or bromine.

The 5-membered heterocyclic ring to which $R^5$ as a quinolinyl, isoquinolinyl or oxodihydroisoquinolinyl group is optionally fused may be, for example, a 5-membered heterocyclic ring having one or two hetero atoms in the ring, said hetero atoms being selected from oxygen, nitrogen and sulfur. Examples of such heterocyclic rings include pyrrole, pyrroline, pyrrolidine, furan, dihydrofuran, tetrahydrofuran, thiophene, dihydrothiophene, tetrahydrothiophene, imidazole, imidazoline, imidazolidine, pyrazole, pyrazoline, pyrazolidine, dioxolane, oxazole, isoxazole, thiazole and isothiazole rings. Preferably the 5-membered heterocyclic ring is a saturated ring having two hetero atoms, preferably two oxygen or two nitrogen atoms, especially two oxygen atoms.

$R^5$ as a quinolinyl group may be a 2-quinolinyl, 3-quinolinyl, 4-quinolinyl, 5-quinolinyl, 6-quinolinyl, 7-quinolinyl or 8-quinolinyl group, preferably a 4-quinolinyl, 5-quinolinyl or 8-quinolinyl group. $R^5$ as an isoquinolinyl group may be a 1-isoquinolinyl, 3-isoquinolinyl, 4-isoquinolinyl, 5-isoquinolinyl, 6-isoquinolinyl, 7-isoquinolinyl, or 8-isoquinolinyl group, preferably a 1-isoquinolinyl or 4-isoquinolinyl group. In most of the especially preferred embodiments of the invention, $R^5$ is a 4-isoquinolinyl group.

$R^5$ as a substituted quinolinyl or isoquinolinyl group is preferably substituted by one, two, three or four of the abovementioned substituents, especially one, two or three of those substituents. The preferred substituted 4-isoquinolinyl group is preferably substituted in the 1- and/or 6- and/or 7- and/or 8-position of the isoquinoline ring system.

In especially preferred embodiments of the invention, $R^5$ is a quinolinyl group of formula

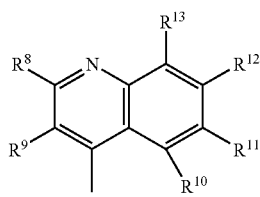

II or an isoquinolinyl group of formula

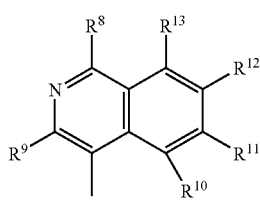

III where $R^8$, $R^9$, $R^{10}$, $R^{11}$, $R^{12}$ and $R^{13}$ are each independently hydrogen or a substituent selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula $—N(R^6)R^7$, aryl optionally substituted by one or more substituents selected from halogen or alkoxy, or heteroaryl having 5 or 6 ring atoms, or $R^{11}$ and $R^{12}$ together with the carbon atoms to which they are attached denote a 5-membered heterocyclic group having two oxygen or nitrogen atoms in the ring, and $R^6$ and $R^7$ are as hereinbefore defined.

$R^5$ as an oxodihydroisoquinolinyl group preferably has the oxo group ortho to the ring nitrogen atom, preferably in the 1-position in the isoquinoline ring system. It is preferably linked to the remainder of the molecule of formula I via the ring carbon atom meta to the ring nitrogen atom, i.e. the 4-position in the isoquinoline ring system. An especially preferred oxodihydroisoquinolinyl group is of formula

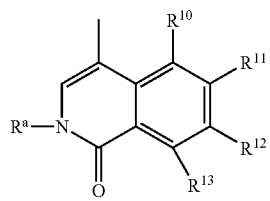

IIIA where $R^{10}$, $R^{11}$, $R^{12}$ and $R^{13}$ are as hereinbefore defined and $R^a$ is hydrogen or $C_1$–$C_4$-alkyl.

Preferred among the compounds of formula I in free or salt form are those where $R^1$ is hydrogen or $C_1$–$C_4$-alkyl optionally substituted by hydroxy, $C_1$–$C_4$-alkoxy or $C_1$–$C_4$-alkylthio, $R^2$ is hydrogen, $C_1$–$C_8$-alkyl, hydroxy-$C_1$–$C_8$-alkyl, $C_1$–$C_4$-alkylcarbonyloxy-$C_1$–$C_8$-alkyl, $C_1$–$C_4$-alkoxy-$C_1$–$C_8$-alkyl, $C_1$–$C_4$-alkylthio-$C_1$–$C_8$-alkyl, $C_2$–$C_4$-alkenyl, $C_3$–$C_8$-cycloalkyl-$C_1$–$C_4$-alkyl, heterocyclyl-$C_1$–$C_4$-alkyl where the heterocyclyl group is a 5- or 6-membered heterocyclyl group having one or two hetero atoms selected from nitrogen and oxygen atoms in the ring, phenyl-$C_1$–$C_4$-alkyl in which the phenyl ring is optionally substituted by one or more substituents selected from $C_1$–$C_4$-alkoxy, amino, $C_1$–$C_4$-alkylamino, di($C_1$–$C_4$-alkyl)amino, $C_1$–$C_4$-alkylcarbonylamino, halogen, $C_1$–$C_4$-alkylsulfonylamino, or di($C_1$–$C_4$-alkyl)aminosulfonylamino, and is optionally fused to a 5-membered heterocyclic ring having two oxygen or two nitrogen atoms in the ring, $R^3$ is hydrogen or $C_1$–$C_4$-alkyl optionally substituted by hydroxy, $C_1$–$C_4$-alkoxy or $C_1$–$C_4$-alkylthio, $R^4$ is hydrogen or $C_1$–$C_4$-alkyl, $R^5$ is a quinolinyl, isoquinolinyl or oxodihydroisoquinolinyl group optionally fused to a 5-membered heterocyclic group having two oxygen or two nitrogen atoms in the ring and optionally substituted by one or more substituents selected from halogen, cyano, carboxy hydroxy, $C_1$–$C_4$-alkyl, hydroxy-$C_1$–$C_4$-alkyl, $C_1$–$C_4$-alkoxy-$C_1$–$C_4$-alkyl, $C_1$–$C_4$-alkylthio-$C_1$–$C_4$-alkyl, $C_1$–$C_4$-alkoxy, $C_1$–$C_4$-alkylthio, $C_2$–$C_4$-alkenyl, $C_2$–$C_4$-alkynyl, $C_1$–$C_4$-alkylcarbonyl, a group $—N(R^6)R^7$ or phenyl optionally substituted by one or more substituents selected from halogen or $C_1$–$C_4$-alkoxy and $R^6$ and $R^7$ are each independently hydrogen or $C_1$–$C_4$-alkyl optionally substituted by hydroxy or alkoxy, or one of $R^6$ and $R^7$ is hydrogen and the other is $C_1$–$C_4$-alkylcarbonyl, or $R^6$ and $R^7$ together with the nitrogen atom to which they are attached denote a 5- or 6-membered heterocyclyl group having one or two nitrogen atoms and, optionally, an oxygen atom in the ring.

Further preferred among the compounds of formula I are those where $R^1$ is hydrogen or $C_1$–$C_4$-alkyl, $R^2$ is hydrogen, $C_1$–$C_8$-alkyl, hydroxy-$C_1$–$C_8$-alkyl, or $C_1$–$C_4$-alkylcarbonyloxy-$C_1$–$C_8$-alkyl, $C_2$–$C_4$-alkenyl, $C_3$–$C_6$-cycloalkyl-$C_1$–$C_4$-alkyl, heterocyclyl-$C_1$–$C_4$-alkyl where the heterocyclyl group is a 5-membered heterocyclyl group having one nitrogen or oxygen atom in the ring, phenyl-$C_1$–$C_4$-alkyl in which the phenyl ring is optionally substituted by one or two substituents selected from $C_1$–$C_4$-alkoxy, amino, $C_1$–$C_4$-alkylcarbonylamino, chlorine, bromine, $C_1$–$C_4$-alkylsulfonylamino, or di($C_1$–$C_4$-alkyl)aminosulfonylamino and is optionally fused to a 5-membered heterocyclic ring having two oxygen atoms in the ring, $R^3$ is hydrogen or $C_1$–$C_4$-alkyl, $R^4$ is hydrogen or $C_1$–$C_4$-alkyl, $R^5$ is a quinolinyl group of formula II, an isoquinolinyl group of formula III or an oxodihydroisoquinolinyl group of formula IIIA, where $R^8$, $R^9$, $R^{10}$, $R^{11}$, $R^{12}$ and $R^{13}$ are each independently selected from hydrogen, halogen, cyano, carboxy, hydroxy, $C_1$–$C_4$-alkyl, hydroxy-$C_1$–$C_4$-alkyl, $C_1$–$C_4$-alkoxy-$C_1$–$C_4$-alkyl, $C_1$–$C_4$-alkylthio$C_1$–$C_4$-alkyl, $C_1$–$C_4$-alkoxy, $C_1$–$C_4$-alkylthio, $C_2$–$C_4$-alkenyl, $C_2$–$C_4$-alkynyl, $C_1$–$C_4$-alkylcarbonyl, a group —N($R^6$)$R^7$ or phenyl optionally substituted by one or two substituents selected from halogen or $C_1$–$C_4$-alkoxy, or $R^{11}$ and $R^{12}$ together with the carbon atoms to which they are attached denote a 5-membered heterocyclic group having two oxygen atoms in the ring, and $R^6$ and $R^7$ are each independently hydrogen or $C_1$–$C_4$-alkyl optionally substituted by hydroxy or alkoxy or one of $R^6$ and $R^7$ is hydrogen and the other is $C_1$–$C_4$-alkylcarbonyl, or $R^6$ and $R^7$ together with the nitrogen atom to which they are attached denote a 6-membered heterocyclyl group having one or two nitrogen atoms, or one nitrogen atom and one oxygen atom, in the ring.

Amongst the further preferred compounds hereinbefore described, especially preferred compounds are usually those in which $R^5$ is an isoquinolinyl group of formula III in which $R^8$ is hydrogen, $C_1$–$C_4$-alkyl, halogen, cyano, —N($R^6$)$R^7$ where $R^6$ and $R^7$ are independently $C_1$–$C_4$-alkyl or $R^6$ and $R^7$ together with the nitrogen atom to which they are attached denote a 6-membered heterocyclyl group having one or two nitrogen atoms, or one nitrogen atom and one oxygen atom, in the ring, or phenyl substituted by one or two $C_1$–$C_4$-alkoxy groups; $R^9$ and $R^{10}$ are each independently hydrogen, $C_1$–$C_4$-alkyl or halogen; $R^{11}$ and $R^{12}$ are each independently hydrogen, halogen, cyano, carboxy, hydroxy, $C_1$–$C_4$-alkyl, $C_1$–$C_4$-alkoxy or $C_2$–$C_4$-alkynyl, or $R^{11}$ and $R^{12}$ together with the carbon atoms to which they are attached denote a 5-membered heterocycle having two oxygen atoms in the ring; and $R^{13}$ is hydrogen or halogen.

Specific especially preferred compounds of formula I are those hereinafter described in the Examples. More preferred amongst these compounds are those of Examples 7, 10, 15, 35, 45, 49, 55, 60, 68 and 70.

According to the present invention preferred combinations are combinations of a PDE 5 inhibitor with an anti-diabetic agent, an anti-hypertensive agent or with both, an anti-diabetic agent and an anti-hypertensive agent, particularly with the active ingredients disclosed as preferred herein.

Especially preferred are combinations of the compound of Example 45 herein with an active ingredient selected from the group consisting of benazepril, benazepril and hydrochlorothiazide, valsartan, valsartan and hydrochlorothiazide, amlodipine, aliskiren, fluvastatin, pitavastatin, hydrochlorothiazide, the DPP IV inhibitors of example 3 of WO 98/19998 and Example 1 of WO 00/34241, respectively, nateglinide, repaglinide and metformin.

The term "at least one active ingredient" as used throughout this specification and in the claims means a combination of a PDE 5 inhibitor with one or more, preferably two or three, active ingredients from one or more, preferably two or three, groups of active ingredients.

Compounds of formula I may be in the form of salts, particularly pharmaceutically acceptable salts. Pharmaceutically acceptable acid addition salts of compounds of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. Pharmaceutically acceptable base salts of compounds of formula I where $R^3$ is hydrogen include metal salts, particularly alkali metal or alkaline earth metal salts such as sodium, potassium, magnesium or calcium salts, and salts with ammonia or pharmaceutically acceptable organic amines or heterocylic bases such as ethanolamines, benzylamines or pyridine. These salts may be prepared from free compounds of formula I or other salts of compounds of formula I by known salt-forming procedures.

PDE5 inhibitors also preferred in the context of the present invention are sildenafil, vardenafil and tadalafil or, in any case, in form of a pharmaceutically acceptable salt. Particularly preferred are PDE5 inhibitors that are marketed, e.g. VIAGRA® which is sildenafil citrate and which can be administered in this form.

Anti-diabetic agents include insulin secretion enhancers which are active ingredients that have the property to promote the secretion of insulin from pancreatic β-cells. Examples of insulin secretion enhancers are a biguanide derivative, for example, metformin or, if appropriate, a pharmaceutically acceptable salt thereof, especially the hydrochloride thereof. Other insulin secretion enhancers include sulfonylureas (SU), especially those which promote the secretion of insulin from pancreatic β-cells by transmitting signals of insulin secretion via SU receptors in the cell membrane, including (but are not limited to) tolbutamide; chlorpropamide; tolazamide; acetohexamide; 4-chloro-N-[(1-pyrolidinylamino)carbonyl]-benzenesulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or pharmaceutically acceptable salts thereof.

Insulin secretion enhancers furthermore include short-acting insulin secretion enhancers, such as the phenylalanine derivative nateglinide [N-(trans-4-isopropylcyclohexylcarbonyl)-D-phenylalanine] (cf. EP 196222 and EP 526171) of the formula

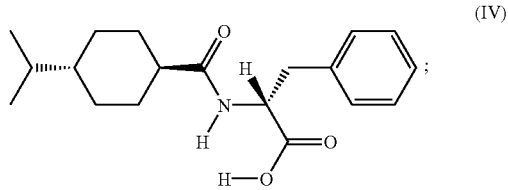

and repaglinide [(S)-2-ethoxy-4-{2-[[3-methyl-1-[2-(1-piperidinyl)phenyl]butyl]amino]-2-oxoethyl}benzoic acid]. Repaglinide is disclosed in EP 589874, EP 147850 A2, in particular Example 11 on page 61, and EP 207331 A1. It can be administered in the form as it is marketed, e.g. under the trademark NovoNorm™; calcium (2S)-2-benzyl-3-(cis-hexahydro-2-isoindolinlycarbonyl)-propionate dihydrate (mitiglinide—cf. EP 507534); furthermore representatives of the new generation of SUs such as glimepiride (cf. EP 31058); in free or pharmaceutically acceptable salt form. The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 of said U.S. patent (referring to H-form crystal modification) as well as the corresponding references to the B-type crystal modification in EP 196222 B1 the subject matter of which, especially with respect to the identification, manufacture and characterization of the B-form crystal modification. Preferably, in the present invention, the B- or H-type, more preferably the H-type, is used. Nateglinide can be administered in the form as it is marketed e.g. under the trademark STARLIX™.

Insulin secretion enhancers likewise include the long-acting insulin secretion enhancer DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is a insulinotropic proteine which was described, e.g., by W. E. Schmidt et al. in Diabetologia 28, 1985, 704–707 and in U.S. Pat. No. 5,705,483.

The term "GLP-1 agonists" used herein means variants and analogs of GLP-1(7-36)NH$_2$ which are disclosed in particular in U.S. Pat. No. 5,120,712, U.S. Pat. No. 5,118, 666, U.S. Pat. No. 5,512,549, WO 91/11457 and by C. Orskov et al in J. Biol. Chem. 264 (1989) 12826. The term "GLP-1 agonists" comprises especially compounds like GLP-1(7-37), in which compound the carboxy-terminal amide functionality of Arg$^{36}$ is displaced with Gly at the 37$^{th}$ position of the GLP-1(7–36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al in Diabetologia 1999, 42, 45–50.

An insulin sensitivity enhancer restores impaired insulin receptor function to reduce insulin resistance and consequently enhance the insulin sensitivity.

An appropriate insulin sensitivity enhancer is, for example, an appropriate hypoglycemic thiazolidinedione derivative (glitazone).

An appropriate glitazone is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methylcyclohexyl)methoxy)-phenyl]methyl}-thiazolidine-2,4-dione (ciglitazone), 5-{[4-(2-(1-indolyl)ethoxy)phenyl] methyl}-thiazolidine-2,4-dione (DRF2189), 5-{4-[2-(5-methyl-2-phenyl-4-oxazolyl)-ethoxy)]benzyl}-thiazolidine-2,4-dione (BM-13. 1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297). Preferred are pioglitazone, rosiglitazone and troglitazone.

Other anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARγ/PPARα agonists; antidiabetic vanadium containing compounds; incretin hormones, like glucagon-like peptide-1 (GLP-1) and GLP-1 agonists; β-cell imidazoline receptor antagonists; miglitol; and α$_2$-adrenergic antagonists; in which the active ingredients are present in each case in free form or in the form of a pharmaceutically acceptable salt.

The term "insulin signalling pathway modulators" as defined herein relates in particular to inhibitors of PTPase, antidiabetic non-small molecule mimetic compounds and inhibitors of GFAT.

Examples of "inhibitors of PTPase" include, but are not limited to those disclosed in U.S. Pat. No. 6,057,316, U.S. Pat. No. 6,001,867, WO 99/58518, WO 99/58522, WO 99/46268, WO 99/46267, WO 99/46244, WO 99/46237, WO 99/46236, WO 99/15529 and by Poucheret et al in Mol. Cell Biochem. 1998, 188, 73–80.

The term "antidiabetic non-small molecule mimetic compounds" as defined herein means compounds as disclosed in Science 1999, 284; 974–97, especially L-783,281, and WO 99/58127, especially CLX-901.

Examples of "inhibitors of GFAT" include, but are not limited to those disclosed in Mol. Cell. Endocrinol. 1997, 135(1), 67–77.

The term "compounds influencing a dysregulated hepatic glucose production" as defined herein relates in particular to inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK).

The term "inhibitors of G6Pase" used herein means a compound or composition which reduces or inhibits hepatic gluconeogenesis by decreasing or inhibiting the activity of G6Pase. Examples of such compounds are disclosed in WO 00/14090, WO 99/40062, WO 98/40385, EP682024 and Diabetes 1998, 47, 1630–1636.

The term "inhibitors of F-1,6-BPase" used herein means a compound or composition which reduces or inhibits hepatic gluconeogenesis by decreasing or inhibiting the activity of F-1,6-BPase. Examples of such compounds are disclosed in WO 00/14095, WO 99/47549, WO 98/39344, WO 98/39343 and WO 98/39342.

The term "inhibitors of GP" as used herein means a compound or composition which reduces or inhibits hepatic glycogenolysis by decreasing or inhibiting the activity of GP. Examples of such compounds are disclosed in EP 978279, U.S. Pat. No. 5,998,463, WO 99/26659, EP 846464, WO 97/31901, WO 96/39384, WO9639385 and in particular CP-91149 as described in Proc. Natl. Acad Sci USA 1998, 95, 1776–1781.

The term "glucagon receptor antagonists" as used herein relates in particular to the compounds described in WO 98/04528, especially BAY27-9955, and those described in Bioorg Med. Chem. Lett 1992, 2, 915–918, especially CP-99,711, J. Med. Chem. 1998, 41, 5150–5157, especially NNC 92-1687, and J. Biol Chem. 1999, 274; 8694–8697, especially L-168,049 and compounds disclosed in U.S. Pat. No. 5,880,139, WO 99/01423, U.S. Pat. No. 5,776,954, WO 98/22109, WO 98/22108, WO 98/21957 and WO 97/16442.

The term "inhibitors of PEPCK" used herein means a compound or composition which reduces or inhibits hepatic gluconeogenesis by decreasing or inhibiting the activity of PEPCK. Examples of such compounds are disclosed in U.S. Pat. No. 6,030,837 and Mol. Biol. Diabetes 1994, 2, 283–99.

The term "PDHK inhibitors" as used herein means inhibitors of pyruvate dehydrogenase kinase and include, but are not limited to, those compounds disclosed by Aicher et al in J. Med. Chem. 42 (1999) 2741–2746.

Examples of "inhibitors of gastric emptying" other than GLP-1 include, but are not limited to those disclosed in J. Clin. Endocrinol. Metab. 2000, 85(3), 1043–1048, especially CCK-8, and in Diabetes Care 1998; 21; 897–893, especially Amylin and analogs thereof, e.g. Pramlintide. Amylin is also described e.g. by O. G. Kolterman et al. in Diabetologia 39, 1996, 492–499.

Insulin is available from different providers under different tradenames, e.g. Berlinsulin© (Berlin-Chemie), Huminsulin© (Eli Lilly), Insulin Actrapid© (Novo Nordisk) or Insuman© (Aventis).

Examples of "inhibitors of GSK-3" include, but are not limited to those disclosed in WO 00/21927 and WO 97/41854.

By "RXR agonist" is meant a compound or composition which when combined with RXR homodimers or heterodimers increases the transcriptional regulation activity of RXR, as measured by an assay known to one skilled in the art, including, but not limited to, the "co-transfection" or "cis-trans" assays described or disclosed in U.S. Pat. Nos. 4,981,784, 5,071,773, 5,298,429, 5,506,102, WO89/05355, WO91/06677, WO92/05447, WO93/11235, WO95/18380, PCT/US93/04399, PCT/US94/03795 and CA 2,034,220, which are incorporated by reference herein. It includes, but is not limited to, compounds that preferentially activate RXR over RAR (i.e. RXR specific agonists), and compounds that activate both RXR and RAR (i.e. pan agonists). It also includes compounds that activate RXR in a certain cellular context but not others (i.e. partial agonists). Compounds disclosed or described in the following articles, patents and patent applications which have RXR agonist activity are incorporated by reference herein: U.S. Pat. Nos. 5,399,586 and 5,466,861, WO96/05165, PCT/US95/16842, PCT/US95/16695, PCT/US93/10094, WO94/15901, PCT/US92/11214, WO93/11755, PCT/US93/10166, PCT/US93/10204, WO94/15902, PCT/US93/03944, WO93/21146, provisional applications 60/004,897 and 60/009,884, Boehm, et al. J. Med. Chem. 38(16):3146–3155, 1994, Boehm, et al. J. Med. Chem. 37(18):2930–2941, 1994, Antras et al., J. Biol. Chem. 266: 157–1161 (1991), Salazar-Olivo et al., Biochem. Biophys. Res. Commun. 204:157–263 (1994) and Safanova, Mol. Cell. Endocrin. 104:201–211 (1994). RXR specific agonists include, but are not limited to, LG 100268 (i.e. 2-[1-(3,5,5,8,8-pentamethyl-5,6,7,8-tetrahydro-2-naphthyl)-cyclopropyl]-pyridine-5-carboxylic acid) and LGD 1069 (i.e. 4-[(3,5,5,8,8-pentamethyl-5,6,7,8-tetrahydro-2-naphthyl)-2-carbonyl]-benzoic acid), and analogs, derivatives and pharmaceutically acceptable salts thereof. The structures and syntheses of LG 100268 and LGD 1069 are disclosed in Boehm, et al. J. Med. Chem. 38(16):3146–3155, 1994, incorporated by reference herein. Pan agonists include, but are not limited to, ALRT 1057 (i.e. 9-cis retinoic acid), and analogs, derivatives and pharmaceutically acceptable salts thereof.

Examples of "agonists of Beta-3 AR" include, but are not limited to CL-316,243 (Lederle Laboratories) and those disclosed in WO 99/29672, WO 98/32753, WO 98/20005, WO 98/09625, WO 97/46556, WO 97/37646 and U.S. Pat. No. 5,705,515.

The term "agonists of UCPs" used herein means agonists of UCP-1, preferably UCP-2 and even more preferably UCP-3. UCPs are disclosed in Vidal-Puig et al., Biochem. Biophys. Res. Commun., Vol. 235(1) pp. 79–82 (1997). Such agonists are a compound or composition which increases the activity of UCPs.

"Non-glitazone type PPARγ agonists" are especially N-(2-benzoylphenyl)-L-tyrosine analogues, e.g. GI-262570, and JTT501.

The term "dual PPARγ/PPARα agonists" as used herein means compounds which are at the same time PPARγ and PPARα agonists. Preferred dual PPARγ/PPARα agonists are especially those ω-[(oxoquinazolinylalkoxy)phenyl]alkanoates and analogs thereof, the compound NN622 described in U.S. Pat. No. 6,054,453, example 22; very especially the compound DRF-554158, also designated DRF 4158, described in WO 99/20614 having the following structure

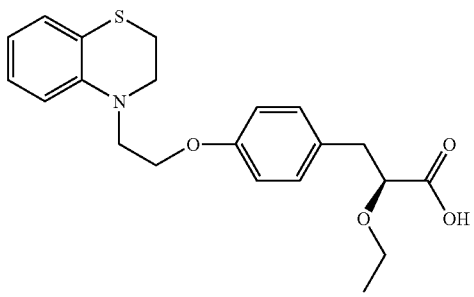

and the compound NC-2100 described by Fukui in Diabetes 2000, 49(5), 759–767.

Preferably, the "antidiabetic vanadium containing compound" is a physiologically tolerable vanadium complex of a bidentate monoprotic chelant, wherein said chelant is an α-hydroxypyrone or α-hydroxypyridinone, especially those disclosed in the Examples of U.S. Pat. No. 5,866,563, of which the working examples are hereby incorporated by reference, or a pharmaceutically acceptable salt thereof.

The term "incretin hormones" as used herein relates in particular to glucagon-like peptide-1 (GLP-1) or GLP-1 agonists.

The term "β-cell imidazoline receptor antagonists" as used herein means compounds as those described in WO 00/78726 and by Wang et al in J. Pharmacol. Exp. Ther. 1996; 278; 82–89, e.g. PMS 812.

Miglitol is (2R, 3R, 4R, 5S)-1-(2-hydroxyethyl)-2-(hydroxymethyl)-3,4,5-piperidinetriol and is described in U.S. Pat. No. 4,639,436. The 1-deoxynojirimycin derivative miglitol can be administered in the form as it is marketed e.g. under the trademark DIASTABOL 50™.

Examples of "α$_2$-adrenergic antagonists" include, but are not limited to midaglizole described in Diabetes 36, 1987, 216–220.

The insulin signalling pathway modulators, compounds influencing a dysregulated hepatic glucose production, pyruvate dehydrogenase kinase (PDHK) inhibitors, inhibitors of gastric emptying, inhibitors of GSK-3, retinoid X receptor (RXR) agonists, agonists of Beta-3 AR, agonists of UCPs, non-glitazone type PPARγ agonists, dual PPARγ/PPARα agonists, antidiabetic vanadium containing compounds, incretin hormones, β-cell imidazoline receptor antagonists, miglitol, and α$_2$-adrenergic antagonists are in each case generically and specifically disclosed in the documents cited above, in each case in particular in the compound claims and the final products of the working examples, the subject-matter of the final products, the pharmaceutical preparations and the claims are hereby incorporated into the present application by reference to these publications. Comprised are likewise the corresponding stereoisomers as well as the corresponding crystal modifications, e.g. solvates and polymorphs, which are disclosed therein and, where applicable, all pharmaceutically acceptable salts thereof.

Any person skilled in the art is fully enabled to identify the active agents and, based on the cited references, likewise enabled to manufacture and test the pharmaceutical indications and properties in standard test models, both in vitro and in vivo.

HMG-Co-A reductase inhibitors (also called β-hydroxy-β-methylglutaryl-co-enzyme-A reductase inhibitors) are understood to be those active agents that may be used to lower the lipid levels including cholesterol, especially LDL-cholesterol, in blood.

The class of HMG-Co-A reductase inhibitors comprises compounds having differing structural features. For example, mention may be made of the compounds that are selected from the group consisting of atorvastatin (cf. EP 680320), cerivastatin (cf. EP 491226), fluvastatin (cf. U.S. Pat. No. 5,354,772), pitavastatin (cf. EP 304063), lovastatin (cf. EP 22478), pravastatin (cf. UK 2077264), rosuvastatin (S 4522) (Wantanabe M., Bioorganic and Medicinal Chemistry (1997) Vol. 5(2) pp. 437–444) and simvastatin (cf. EP 33538), or, in each case, a pharmaceutically acceptable salt thereof.

Preferred HMG-Co-A reductase inhibitors are those agents that have been marketed, most preferred is fluvastatin, atorvastatin, pravastatin, or simvastatin and also pitavastatin or, in each case, a pharmaceutically acceptable salt thereof.

Anti-hypertensive agents include angiotensin converting enzyme inhibitors (ACE-inhibitors) and AT$_1$ receptor antagonists. The interruption of the enzymatic degradation of angiotensin I to angiotensin II with ACE-inhibitors is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril (cf. EP 7477), benazepril (cf. EP 72352), benazeprilat (cf. EP 72352), captopril (cf. U.S. Pat. No. 4,105,776), ceronapril (cf. EP 229520), cilazapril (cf. EP 94095), delapril (cf. EP 51391), enalapril (cf. EP 12401), enaprilat (cf. EP 12401), fosinopril (cf. EP 53902), imidapril (cf. EP 95163), lisinopril (cf. EP 12401), moveltipril (cf. ZA 82/3779), perindopril (cf. EP 49658), quinapril (cf. EP 49605), ramipril (cf. EP 79022), spirapril (cf. EP 50800), temocapril (cf. EP 161801), and trandolapril (cf. EP 551927), or, in each case, a pharmaceutically acceptable salt thereof.

Preferred ACE inhibitors are those agents that have been marketed, most preferred are benazepril, enalapril and lisinopril.

The corresponding active ingredients or pharmaceutically acceptable salts thereof may also be used in form of a solvate, such as a hydrate or including other solvents, used for crystallization.

The class of AT$_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

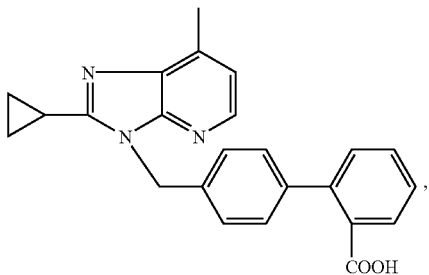

the compound with the designation SC-52458 of the following formula

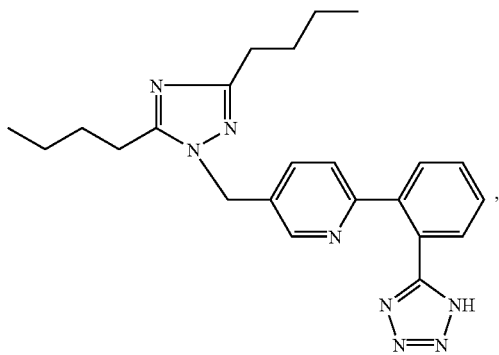

and the compound with the designation the compound ZD-8731 of the following formula

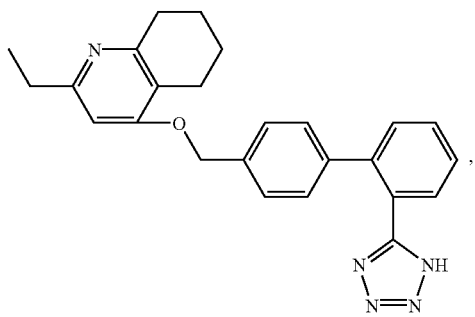

or, in each case, a pharmaceutically acceptable salt thereof.

Preferred $AT_1$-receptor antagonist are those agents which have been marketed, most preferred is valsartan or a pharmaceutically acceptable salt thereof.

Anti-hypertensive agents also include renin inhibitors. Renin inhibitors include especially non-peptidic representatives, preferably aliskiren (2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy) phenyl]-octanamide, being specifically disclosed in EP 678503 A); especially preferred is the hemi-fumarate salt thereof; detikiren (cf. EP 173481A); terlakiren (cf. EP 266950 A); and zankiren (cf. EP 229667 A). Especially preferred is aliskiren, preferably the hemi-fumarate thereof.

Additional anti-hypertensive agents include adrenergic blockers, diuretics, e.g. hydrochlorothiazide, neutral endopeptidases inhibitors, endothelin converting enzyme inhibitors, endothelin receptor antagonists, adrenergic stimulants, alpha/beta adrenergic blockers beta adrenergic blocking agents, calcium channel blockers, rauwolfia derivatives and vasodilators or any combination thereof.

Adrenergic blockers include propranolol, bisoprolol and metoprolol.

Examples of calcium channel blockers useful in the combinations of the present invention are selected from the group consisting of diltiazem, nifedipine, nitrendipine, nimodipine, niludipine, niguldipine, nicardipine, nisoldipine, amlodipine, felodipine, isradipine, ryosidine, verapamil, gallopamil and tiapamil or in each case a pharmaceutically acceptable salt thereof.

Preferred calcium channel blockers are those which are marketed, especially amlodipine.

Serotonin reuptake inhibitors (SSRIs), include, for example, fluvoxamine; fluoxetine; paroxetine; sertraline; citalopram; venlafaxine; cericlamine; duloxetine; milnaciperan; nefazodone; and cyanodothiepin (See The Year Drugs News, 1995 Edition, pp. 47–48 by Prous J. R.) and WO 97/29739.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The following Examples further illustrate the invention with respect to specific PDE5 inhibitors. The preparation of the compounds of these Examples, their intermediates and their analytical characterization is disclosed in WO 01/77110, the whole content of which is being incorporated by reference herewith.

EXAMPLES 1–87

Compounds of Formula I which are also of Formula

V

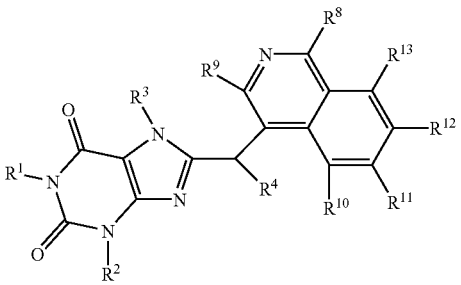

where $R^1$ to $R^4$ and $R^8$ to $R^{13}$ are as hereinbefore defined, in free or salt form, and their methods of preparation are shown in the following table, the methods being described hereinafter. $R^3$ is H in all Examples except No 44, where it is $CH_3$. $R^4$ is H in all examples except Nos 25–27 and 41–43, where it is $CH_3$. $R^9$ is H in all Examples except No 29, where it is $CH_3$. $R^{10}$ is H in all Examples except No 57, where it is Br and No 75 where it is Cl. $R^{13}$ is H in all Examples except Nos 56 where it is F, and 65 and 66, where it is Br.

| Ex. No. | R¹ | R² | R⁸ | R¹¹ | R¹² |
|---|---|---|---|---|---|
| 1 | CH₃ | (CH₃)₂CHCH₂ | 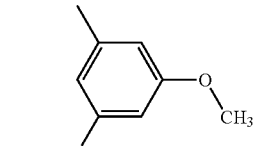 | OCH₃ | OCH₃ |
| 2 | CH₃ | (CH₃)₂CHCH₂ | 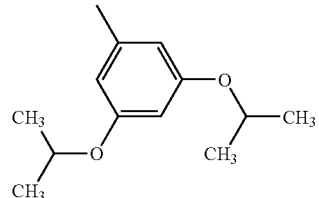 | OCH₃ | OCH₃ |
| 3 | CH₃ | (CH₃)₂CHCH₂ | 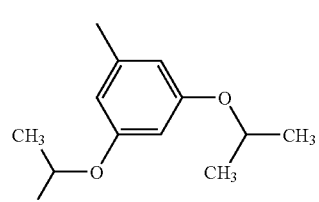 | OCH(CH₃)₂ | OCH₃ |
| 4 | CH₃ | (CH₃)₂CHCH₂ | 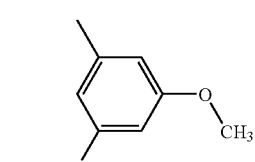 | OCH(CH₃)₂ | OCH₃ |
| 5 | CH₃ | (CH₃)₂CHCH₂ | (CH₃)₃C | OCH(CH₃)₂ | OCH₃ |
| 6 | CH₃ | (CH₃)₂CHCH₂ | (CH₃)₂CH | OCH(CH₃)₂ | OCH₃ |
| 7 | CH₃ | (CH₃)₂CHCH₂ | CH₃ | OCH₃ | OCH₃ |
| 8 | CH₃ | (CH₃)₂CHCH₂ | (CH₃)₃C | OCH₃ | OCH₃ |
| 9 | CH₃ | (CH₃)₂CHCH₂ | (CH₃)₂CH | OCH₃ | OCH₃ |
| 10 | CH₃ | (CH₃)₂CHCH₂ | H | OCH₃ | OCH₃ |
| 11 | CH₃ | 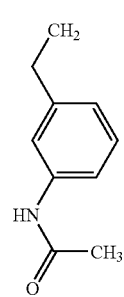 | H | OCH₃ | OCH₃ |
| 12 | H | CH₃ | H | OCH₃ | OCH₃ |
| 13 | CH₃ | CH₂=CHCH₂ | H | OCH₃ | OCH₃ |
| 14 | CH₃ | 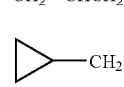 | H | OCH₃ | OCH₃ |
| 15 | CH₃ | (CH₃)₃CCH₂ | H | OCH₃ | OCH₃ |
| 16 | (CH₃)₂CHCH₂ | (CH₃)₂CHCH₂ | H | OCH₃ | OCH₃ |
| 17 | CH₃ | 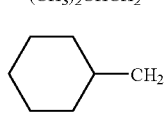 | H | OCH₃ | OCH₃ |

-continued
| Ex. No. | R¹ | R² | R⁸ | R¹¹ | R¹² |
|---|---|---|---|---|---|
| 18 | $CH_3$ | $CH_2=C(CH_3)CH_2$ | H | $OCH_3$ | $OCH_3$ |
| 19 | $CH_3$ | 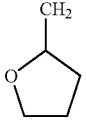 | H | $OCH_3$ | $OCH_3$ |
| 20 | $CH_3$ | 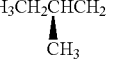 | H | $OCH_3$ | $OCH_3$ |
| 21 | H | $CH_3CH_2CH_2$ | H | $OCH_3$ | $OCH_3$ |
| 22 | $CH_3$ | 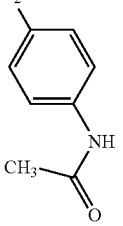 | H | $OCH_3$ | $OCH_3$ |
| 23 | $CH_3$ | $(CH_3)_2CHCH_2$ | H |  | |
| 24 | $CH_3$ | $(CH_3)_2CHCH_2$ | H | H | $OCH_3$ |
| 25 | $CH_3$ | $(CH_3)_2CHCH_2$ | Cl | H | $OCH_3$ |
| 26 | $CH_3$ | $(CH_3)_2CHCH_2$ | CN | H | $OCH_3$ |
| 27 | $CH_3$ | $(CH_3)_2CHCH_2$ | 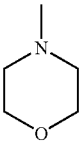 | H | $OCH_3$ |
| 28 | $CH_3$ | $(CH_3)_2CHCH_2$ | H | $OCH_3$ | OH |
| 29 | $CH_3$ | $(CH_3)_2CHCH_2$ | H | $OCH_3$ | $OCH_3$ |
| 30 | $CH_3$ | $CH_3(CH_2)_5$ | H | $OCH_3$ | $OCH_3$ |
| 31 | $CH_3$ | 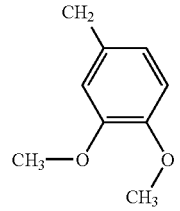 | H | $OCH_3$ | $OCH_3$ |
| 32 | $CH_3$ | 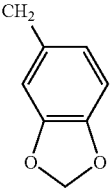 | H | $OCH_3$ | $OCH_3$ |

-continued

| Ex. No. | R¹ | R² | R⁸ | R¹¹ | R¹² |
|---|---|---|---|---|---|
| 33 | CH₃ | 2,4-dichlorobenzyl (CH₂-C₆H₃(Cl)₂) | H | OCH₃ | OCH₃ |
| 34 | CH₃ | 4-methoxy-methylbenzyl | H | OCH₃ | OCH₃ |
| 35 | CH₃ | (CH₃)₂CHCH₂ | Cl | OCH₃ | OCH₃ |
| 36 | CH₃ | (CH₃)₂CHCH₂ | H | H | H |
| 37 | CH₃ | (CH₃)₂CHCH₂ | H | OCH₂CH₃ | OCH₃ |
| 38 | CH₃ | (CH₃)₂CHCH₂ | N-morpholinyl | OCH₃ | OCH₃ |
| 39 | CH₃ | (CH₃)₂CHCH₂ | 4-methylpiperazin-1-yl | OCH₃ | OCH₃ |
| 40 | CH₃ | (CH₃)₂CHCH₂ | H | OCH₃ | OCH₂CH₂ |
| 41 | CH₃ | (CH₃)₂CHCH₂ | H | OCH₂CH₃ | OCH₃ |
| 42 | CH₃ | (CH₃)₂CHCH₂ | H | OCH₃ | OCH₂CH₃ |
| 43 | CH₃ | (CH₃)₂CHCH₂ | H | OCH₃ | OCH₃ |
| 44 | CH₃ | (CH₃)₂CHCH₂ | H | OCH₃ | OCH₃ |
| 45 | CH₃ | (CH₃)₂CHCH₂ | H | OCH₃ | H |
| 46 | CH₃ | CH₃CH₂CH(CH₃)CH₂ | H | OCH₃ | H |
| 47 | CH₃ | (CH₃)₂CCH₂ | H | Cl | H |
| 48 | CH₃ | (CH₃)₂CHCH₂ | H | Cl | H |
| 49 | CH₃ | cyclopropyl-CH₂ | H | OCH₃ | H |
| 50 | CH₃ | cyclopropyl-CH₂ | H | Cl | H |
| 51 | CH₃ | cyclobutyl-CH₂ | H | OCH₃ | OCH₃ |
| 52 | CH₃ | CH₂=C(CH₃)CH₂ | H | OCH₃ | H |
| 53 | CH₃ | (CH₃)₂CHCH₂ | H | Br | H |
| 54 | CH₃ | (CH₃)₃CCH₂ | H | OCH₃ | H |
| 55 | CH₃ | (CH₃)₂CHCH₂ | H | C≡CH | H |
| 56 | CH₃ | (CH₃)₂CHCH₂ | H | OCH₃ | H |
| 57 | CH₃ | (CH₃)₂CHCH₂ | H | OCH₃ | H |

-continued

| Ex. No. | $R^1$ | $R^2$ | $R^8$ | $R^{11}$ | $R^{12}$ |
|---|---|---|---|---|---|
| 58 | $CH_3$ | 3-(aminomethyl... 3-ethylaniline (3-ethylphenyl with NH₂) | H | $OCH_3$ | $OCH_3$ |
| 59 | $CH_3$ | 3-ethylphenyl-NH-S(O)₂-N(CH₃)₂ | H | $OCH_3$ | $OCH_3$ |
| 60 | $CH_3$ | 4-ethylphenyl-NH-S(O)₂-N(CH₃)₂ | H | $OCH_3$ | $OCH_3$ |
| 61 | $CH_3$ | 4-ethylphenyl-NH-S(O)₂-CH(CH₃)₂ | H | $OCH_3$ | $OCH_3$ |
| 62 | $CH_3$ | 4-ethylaniline (4-ethylphenyl with NH₂) | H | $OCH_3$ | $OCH_3$ |
| 63 | $CH_3$ | $(CH_3)_2CHCH_2$ | H | H | OH |
| 64 | $CH_3$ | $(CH_3)_2CHCH_2$ | H | OH | OH |
| 65 | $CH_3$ | $(CH_3)_2CHCH_2$ | H | OH | OH |
| 66 | $CH_3$ | $(CH_3)_2CHCH_2$ | H | H | OH |
| 67 | $CH_3$ | $HO(CH_2)_3$ | H | $OCH_3$ | $OCH_3$ |
| 68 | $CH_3$ | 2-methylbutan-1-ol (CH₃CH₂CH(CH₃)CH₂OH) | H | $OCH_3$ | $OCH_3$ |
| 69 | $CH_3$ | 2-methylbutyl acetate (CH₃CH₂CH(CH₃)CH₂OC(O)CH₃) | H | $OCH_3$ | $OCH_3$ |

-continued

| Ex. No. | R¹ | R² | R⁸ | R¹¹ | R¹² |
|---|---|---|---|---|---|
| 70 | $CH_3$ | 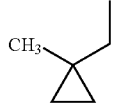 | H | $OCH_3$ | $OCH_3$ |
| 71 | $CH_3$ | 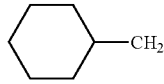 | H | $OCH_3$ | H |
| 72 | $CH_3$ | 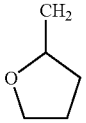 | H | $OCH_3$ | H |
| 73 | $CH_3$ | $(CH_3)_2CHCH_2$ | H | $OCH_3$ | F |
| 74 | $CH_3$ | $(CH_3)_2CHCH_2$ | H | $CO_2H$ | H |
| 75 | $CH_3$ | $(CH_3)_2CHCH_2$ | H | $OCH_3$ | H |
| 76 | $CH_3$ | $(CH_3)_2CHCH_2$ | H | CN | H |
| 77 | $CH_3$ | $(CH_3)_2CHCH_2$ | H | $CH_2CH_3$ | H |
| 78 | $CH_3$ | $(CH_3)_2CHCH_2$ | H | $OCH_2CH_3$ | H |
| 79 | $CH_3$ | 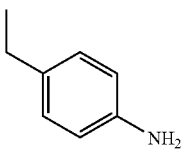 | H | $OCH_3$ | H |
| 80 | $CH_3$ | 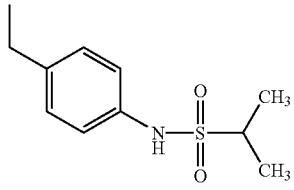 | H | $OCH_3$ | H |
| 81 | $CH_3$ | 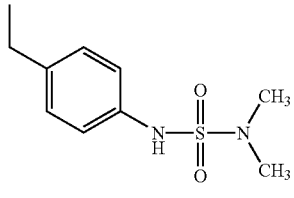 | H | $OCH_3$ | H |
| 82 | $CH_3$ | $(CH_3)_2CHCH_2$ | $N(CH_2)_3$ | $OCH_3$ | $OCH_3$ |
| 83 | $CH_3$ | $(CH_3)_2CHCH_2$ | 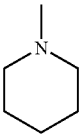 | $OCH_3$ | $OCH_3$ |
| 83 | $CH_3$ | $(CH_3)_2CHCH_2$ | $CH_3$ | $OCH_3$ | H |
| 84 | $CH_3$ | $(CH_3)_2CHCH_2$ | $CH_3$ | $OCH(CH_3)_2$ | H |
| 85 | $CH_3$ | $(CH_3)_2CHCH_2$ | $CH_3$ | $OCH_2CH_3$ | H |

Example 86

3-Isobutyl-1-methyl-8-[1-(6-methyl-5-oxo-5,6-dihydro-[1,3]dioxolo[4,5-.g.]isoquinolin-8-yl)-ethyl]-3,7-dihydro-purine-2,6-dione

Example 87

8-(6,7-Dimethoxy-quinolin-4-ylmethyl)-3-isobutyl-1-methyl-3,7-dihydro-purine-2,6-dione Another aspect of the present invention relates to the prevention, delay of progression or treatment of a condition or disease selected from the group consisting of sexual dysfunction, a cardiovascular disease or disorder, a diabetic disease or disorder, a hyperlipidemic disease or disorder, and a metabolic disease or disorder comprising administration of a therapeutically effective amount of a pharmaceutical composition comprising
(a) PDE 5 inhibitor or a pharmaceutically acceptable salt thereof and
(b) at least one active ingredient selected from the group consisting of
  (i) an anti-diabetic agent;
  (ii) HMG-Co-A reductase inhibitors;
  (iii) an anti-hypertensive agent; and
  (iv) a serotonin reuptake inhibitor (SSRI)
or, in each case, a pharmaceutically acceptable salt thereof;
to a warm-blooded mammal in need thereof.

Another aspect of the present invention relates to the treatment of sexual dysfunction, especially male erectile dysfunction (MED) and a cardiovascular disease or disorder comprising administration of a therapeutically effective amount of a pharmaceutical composition comprising a PDE5 inhibitor and an anti-hypertensive agent to a warm-blooded mammal in need thereof. To evaluate the antihypertensive activity of the combination according to the invention, for example, the methodology as described by Lovenberg W: Animal models for hypertension research. Prog. Clin. Biol. Res. 1987, 229, 225–240 may be applied. For the evaluation that the combination according to the present invention may be used for the treatment of congestive heart failure, for example, the methods as disclosed by Smith H J, Nuttall A: Experimental models of heart failure. Cardiovasc Res 1985, 19, 181–186 may be applied. Molecular approaches such as transgenic methods are also described, for example by Luft et al.: Hypertension-induced end-organ damage. A new transgemic approach for an old problem. Hypertension 1999, 33, 212–218.

Another aspect of the present invention relates to the treatment of MED and a diabetic disease or disorder comprising administration of a therapeutically effective amount of a pharmaceutical composition comprising a PDE5 inhibitor and an anti-diabetic agent to a warm-blooded mammal in need thereof. The insulin secretion enhancing properties of the combination according to the present invention may be determined by following the methodology as disclosed, for example, in the publication of Tlkenoue et al. Biol. Pharm. Bull. 29(4), 354–359 (1997).

Another aspect of the present invention relates to the treatment of MED and a hyperlipidemic disease or disorder comprising administration of a therapeutically effective amount of a pharmaceutical composition comprising a PDE5 inhibitor and an HMG-CoA reductase inhibitor to a warm-blooded mammal in need thereof. To evaluate the HMG-Co-A reductase inhibitory activities of the combination according to the invention, for example, may be determined by following the methodology as disclosed, for example, in U.S. Pat. No. 4,739,073 or U.S. Pat. No. 5,354,772, respectively. The corresponding subject matter of these two references is herewith incorporated by reference in this specification.

In yet another aspect of the present invention relates to the treatment of MED and a metabolic disease or disorder comprising administration of a therapeutically effective amount of a pharmaceutical composition comprising a PDE5 inhibitor and an SSRI to a warm-blooded mammal in need thereof.

The pharmaceutical activities as effected by administration of the combination of active agents used according to the present invention can be demonstrated e.g. by using corresponding pharmacological models known in the pertinent art. The person skilled in the pertinent art is fully enabled to select a relevant animal test model to prove the hereinbefore and hereinafter indicated therapeutic indications and beneficial effects.

Accordingly, the combination or pharmaceutical composition according to the present invention may be used, e.g., for the prevention, delay of progression or treatment of diseases and disorders selected from those named hereinbefore and hereinafter.

A "cardiovascular disease or disorder" as defined in this application comprises, but is not limited to hypertension, congestive heart failure, diabetes, glomerulosclerosis, chronic and acute renal failure, coronary heart disease, angina pectoris, myocardial infarction, stroke, vascular restenosis endothelial dysfunction, impaired vascular compliance and congestive heart failure.

A "diabetic disease or disorder" as defined in this application comprises, but is not limited to hyperglycemia, hyperinsulinaemia, diabetes, insulin resistance, impaired glucose metabolism, conditions of impaired glucose tolerance (IGT), conditions of impaired fasting plasma glucose, obesity, diabetic retinopathy, diabetic nephropathy, glomerulosclerosis, diabetic neuropathy and syndrome X.

A "hyperlipidemic disease or disorder" as defined in this application comprises, but is not limited to hyperlipidaemia, hypertriglyceridemia, coronary heart disease, vascular restenosis, endothelial dysfunction, obesity and impaired vascular compliance.

A "metabolic disease or disorder" as defined in this application comprises, but is not limited to obesity.

Hypertension, especially in connection with a "cardiovascular disease or condition", includes and is not limited to mild, moderate and severe hypertension as defined in Journal of Hypertension 1999, 17:151–183, especially on page 162. Especially preferred is "isolated systolic hypertension" (ISH).

Preferably, the jointly therapeutically effective amounts of the active agents according to the combination of the present invention can be administered simultaneously or sequentially in any order, e.g. separately or in a fixed combination.

All the more surprising is the experimental finding that the combined administration of a PDE5 inhibitor with an anti-diabetic agent, a HMG-Co A reductase inhibitor, an anti-hypertensive agent and/or an SSRI, in each case, a pharmaceutically acceptable form thereof, results not only in a beneficial, especially a potentiating or a synergistic, therapeutic effect. Independent thereof, additional benefits resulting from combined treatment can be achieved such as a surprising prolongation of efficacy, a broader variety of therapeutic treatment and surprising beneficial effects on diseases and conditions.

The term "potentiation" shall mean an increase of a corresponding pharmacological activity or therapeutical effect, respectively. Potentiation of one component of the combination according to the present invention by co-administration of an other component according to the present invention means that an effect is being achieved that is greater than that achieved with one component alone.

The term "synergistic" shall mean that the drugs, when taken together, produce a total joint effect that is greater than the sum of the effects of each drug when taken alone.

Further benefits are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

The present invention also relates to a method for the prevention, delay of progression or treatment of sexual dysfunction, especially MED, and a diabetic, cardiovascular, metabolic, hyperlipidemic disease and disorder comprising administering to a warm-blooded mammal, including man, in need thereof jointly therapeutically effective amounts of a pharmaceutical composition comprising
(a) a PDE 5 inhibitor or a pharmaceutically acceptable salt thereof and
(b) at least one active ingredient selected from the group consisting of
  (i) an anti-diabetic agent;
  (ii) HMG-Co-A reductase inhibitors;
  (v) an anti-hypertensive agent; and
  (vi) a serotonin reuptake inhibitor (SSRI)
  or, in each case, a pharmaceutically acceptable salt thereof;
and a pharmaceutically acceptable carrier.

Further, the present invention relates to the use of a combination comprising
(a) a PDE 5 inhibitor or a pharmaceutically acceptable salt thereof and
(b) at least one active ingredient selected from the group consisting of
  (i) an anti-diabetic agent;
  (ii) HMG-Co-A reductase inhibitors;
  (vii) an anti-hypertensive agent; and
  (viii) a serotonin reuptake inhibitor (SSRI)
  or, in each case, a pharmaceutically acceptable salt thereof;
for the preparation of an agent for the treatment of sexual dysfunction, especially MED, a diabetic, cardiovascular, metabolic or hyperlipidemic disease and disorder.

The pharmaceutical composition according to the present invention as described hereinbefore and hereinafter may be used for simultaneous use or sequential use in any order, e.g. for separate use or as a fixed combination.

The pharmaceutical composition according to the present invention comprises a "kit of parts" in the sense that the components can be dosed independently or by use of different fixed combinations with distinguished amounts of the components at different time points. The parts of the "kit of parts" can then e.g. be administered simultaneously or chronologically staggered, that is at different time points and with equal or different time intervals for any part of the "kit of parts". Preferably, the time intervals are chosen such that the effect on the treated disease or condition in the combined use of the parts is larger than the effect that would be obtained by use of only any one of the components. Preferably, there is at least one beneficial effect, e.g. a mutual enhancing of the effect of a pharmaceutical composition comprising
(a) a PDE 5 inhibitor or a pharmaceutically acceptable salt thereof and
(b) at least one active ingredient selected from the group consisting of
  (i) an anti-diabetic agent;
  (ii) HMG-Co-A reductase inhibitors;
  (iii) an anti-hypertensive agent; and
  (iv) a serotonin reuptake inhibitor (SSRI)
  or, in each case, a pharmaceutically acceptable salt thereof;
and a pharmaceutically acceptable carrier;
in particular a potentiation or a synergism, e.g. a more than additive effect, additional advantageous effects, less side effects, a combined therapeutic effect in a non-effective dosage of one or each of the components, especially a potentiation or synergism.

The invention furthermore relates to a commercial package comprising the combination according to the present invention together with instructions for simultaneous, separate or sequential use.

These pharmaceutical preparations are for oral administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compounds. These are prepared in a manner that is known per se, for example using conventional mixing, granulation, coating, solubulizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those that are commercially available.

Normally, in the case of oral administration of pharmaceutical composition in accordance with the present invention, an approximate daily dose of from about 1 mg to about 360 mg is to be estimated, preferably a daily dose of from 1 mg to 100 mg, more preferably a daily dose of from 1 mg to 50 mg, e.g. for a patient of approximately 75 kg in weight.

The insulin secretion enhancer repaglinde is preferably administered in a dosage range of about 0.01 mg to about 8 mg, more preferred from about 0.5 to about 6 mg.

In case of HMG-Co-A reductase inhibitors, preferred dosage unit forms of HMG-Co-A reductase inhibitors are, for example, tablets or capsules comprising e.g. from about 5 mg to about 120 mg, preferably, when using fluvastatin, for example, 20 mg, 40 mg or 80 mg (equivalent to the free acid) of fluvastatin, for example, administered once a day.

In case of ACE inhibitors, preferred dosage unit forms of ACE inhibitors are, for example, tablets or capsules comprising e.g. from about 5 mg to about 20 mg, preferably 5 mg, 10 mg, 20 mg or 40 mg, of benazepril; from about 6.5 mg to 100 mg, preferably 6.25 mg, 12.5 mg, 25 mg, 50 mg, 75 mg or 100 mg, of captopril; from about 2.5 mg to about 20 mg, preferably 2.5 mg, 5 mg, 10 mg or 20 mg, of enalapril; from about 10 mg to about 20 mg, preferably 10 mg or 20 mg, of fosinopril; from about 2.5 mg to about 4 mg, preferably 2 mg or 4 mg, of perindopril; from about 5 mg to about 20 mg, preferably 5 mg, 10 mg or 20 mg, of quinapril; or from about 1.25 mg to about 5 mg, preferably 1.25 mg, 2.5 mg, or 5 mg, of ramipril. Preferred is t.i.d. administration.

Valsartan, as a representative of the class of $AT_1$-receptor antagonists, is supplied in the form of suitable dosage unit form, for example, a capsule or tablet, and comprising a therapeutically effective amount, e.g. from about 20 mg to about 320 mg, of valsartan which may be administered to patients, preferably from about 80 mg to about 320 mg. The application of the active ingredient may occur up to three times a day, starting e.g. with a daily dose of 20 mg or 40 mg of valsartan, increasing via 80 mg daily and further to 160 mg daily up to 320 mg daily. Preferably, valsartan is applied twice a day with a dose of 80 mg or 160 mg, respectively, each. Corresponding doses may be taken, for example, in the morning, at mid-day or in the evening. Preferred is b.i.d. administration.

In case of SSRIs, preferred dosage unit forms are, for example, tablets or capsules comprising e.g. from about 20 mg to about 200 mg, administered once a day.

In case of PDE5, preferred dosage unit forms are, for example, tablets or capsules comprising e.g. from about 25 mg to about 200 mg, per dose, with 3-isobutyl-8-(6-methoxy-isoquinolin-4-ylmethyl)-1-methyl-3,7-dihydro-purine-2,6-dione being administered in a dose of about 100 mg to about 200 mg.

Examples of formulations of active ingredients of the present inventions are disclosed in WO 01/76573 and WO 01/76574, respectively, the contents of which being incorporated by reference herewith.

What is claimed is:

1. A pharmaceutical composition comprising a PDE 5 inhibitor of formula

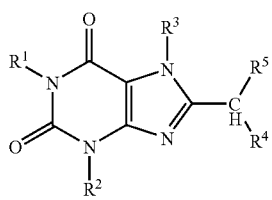

in free or salt form, where
$R^1$ is hydrogen or alkyl optionally substituted by hydroxy, alkoxy, or alkylthio,
$R^2$ is hydrogen, alkyl, hydroxyalkyl, alkylcarbonyloxyalkyl, alkoxyalkyl, alkylthioalkyl, alkenyl, cycloalkylalkyl, heterocyclylalkyl, aralkyl in which the aryl ring thereof is optionally fused to a 5-membered heterocyclic group or is optionally substituted by one or more substituents selected from alkoxy, amino, alkylamino, dialkylamino, acylamino, halogen, hydroxy, aminosulfonyl, alkylaminosulfonyl, dialkylaminosulfonyl, alkylsulfonylamino or dialkylaminosulfonylamino,
$R^3$ is hydrogen or alkyl optionally substituted by hydroxy, alkoxy, or alkylthio,
$R^4$ is hydrogen or alkyl,
$R^5$ is a quinolinyl, isoquinolinyl or oxodihydroisoquinolinyl group optionally fused to a 5-membered heterocyclic group and optionally substituted by one or more substituents selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —N($R^6$)$R^7$, aryl optionally substituted by one or more substituents selected from halogen or alkoxy, or heteroaryl having 5 or 6 ring atoms attached through a ring carbon atom to the indicated carbon atom, and
$R^6$ and $R^7$ are each independently hydrogen or alkyl optionally substituted by hydroxy or alkoxy or one of $R^6$ and $R^7$ is hydrogen and the other is acyl, or $R^6$ and $R^7$ together with the nitrogen atom to which they are attached denote a 5- or 6-membered heterocyclyl group;
and an HMG-Co-A reductase inhibitor and a pharmaceutically acceptable carrier.

2. The pharmaceutical composition of claim 1 wherein the PDE 5 inhibitor is 3-isobutyl-8-(6-methoxy-isoquinolin-4-ylmethyl)-1-methyl-3,7-dihydro-purine-2,6-dione.

3. The pharmaceutical composition of claim 1 wherein the HMG-Co-A reductase inhibitor is selected from the group consisting of atorvastatin, cerivastatin, fluvastatin, pitavastatin, lovastatin, pravastatin, rosuvastatin and simvastatin.

4. The pharmaceutical composition of claim 1 in which $R^5$ is a quinolinyl group of formula

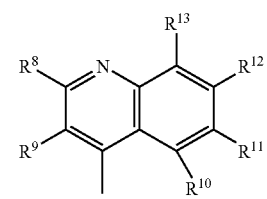

or an isoquinolinyl group of formula

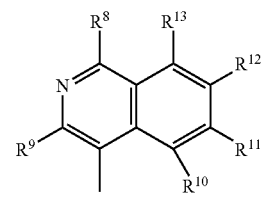

or an oxodihydroisoquinolinyl group of formula

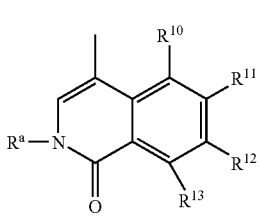

where $R^8$, $R^9$, $R^{10}$, $R^{11}$, $R^{12}$ and $R^{13}$ are each independently hydrogen or a substituent selected from halogen, cyano, hydroxy, alkyl, hydroxyalkyl, alkoxyalkyl, alkylthioalkyl, alkoxy, alkylthio, alkenyl, alkoxycarbonyl, alkynyl, carboxyl, acyl, a group of formula —N(R$^6$)R$^7$, aryl optionally substituted by one or more substituents selected from halogen or alkoxy, or heteroaryl having 5 or 6 ring atoms, and R$^6$ and R$^7$ are each independently hydrogen or alkyl optionally substituted by hydroxy or alkoxy or one of R$^6$ and R$^7$ is hydrogen and the other is acyl, or R$^6$ and R$^7$ together with the nitrogen atom to which they are attached denote a 5- or 6-membered heterocyclyl group, or R$^{11}$ and R$^{12}$ together with the carbon atoms to which they are attached denote a 5-membered heterocyclic group having two oxygen or nitrogen atoms in the ring, and R$^a$ is hydrogen or C$_1$–C$_4$-alkyl.

5. The pharmaceutical composition of claim 4 in which R$^1$ is hydrogen or C$_1$–C$_4$-alkyl, R$^2$ is hydrogen, C$_1$–C$_8$-alkyl, hydroxy-C$_1$–C$_8$-alkyl, or C$_1$–C$_4$-alkylcarbonyloxy-C$_1$–C$_8$-alkyl, C$_2$–C$_4$-alkenyl, C$_3$–C$_6$-cycloalkyl-C$_1$–C$_4$-alkyl, heterocyclyl-C$_1$–C$_4$-alkyl where the heterocyclyl group is a 5-membered heterocyclyl group having one nitrogen or oxygen atom in the ring, phenyl-C$_1$–C$_4$-alkyl in which the phenyl ring is optionally substituted by one or two substituents selected from C$_1$–C$_4$-alkoxy, amino, C$_1$–C$_4$-alkylcarbonylamino, chlorine, bromine, C$_1$–C$_4$-alkylsulfonylamino, or di(C$_1$–C$_4$-alkyl)aminosulfonylamino and is optionally fused to a 5-membered heterocyclic ring having two oxygen atoms in the ring, R$^3$ is hydrogen or C$_1$–C$_4$-alkyl, R$^4$ is hydrogen or C$_1$–C$_4$-alkyl, R$^5$ is a quinolinyl group of formula II, an isoquinolinyl group of formula III or an oxodihydroisoquinolinyl group of formula IIIA, where R$^8$, R$^9$, R$^{10}$, R$^{11}$, R$^{12}$ and R$^{13}$ are each independently selected from hydrogen, halogen, cyano, carboxy, hydroxy, C$_1$–C$_4$-alkyl, hydroxy-C$_1$–C$_4$-alkyl, C$_1$–C$_4$-alkoxy-C$_1$–C$_4$-alkyl, C$_1$–C$_4$-alkylthioC$_1$–C$_4$-alkyl, C$_1$–C$_4$-alkoxy, C$_1$–C$_4$-alkylthio, C$_2$–C$_4$-alkenyl, C$_2$–C$_4$-alkynyl, C$_1$–C$_4$-alkylcarbonyl, a group —N(R$^6$)R$^7$ or phenyl optionally substituted by one or two substituents selected from halogen or C$_1$–C$_4$-alkoxy, or R$^{11}$ and R$^{12}$ together with the carbon atoms to which they are attached denote a 5-membered heterocyclic group having two oxygen atoms in the ring, and R$^6$ and R$^7$ are each independently hydrogen or C$_1$–C$_4$-alkyl optionally substituted by hydroxy or alkoxy or one of R$^6$ and R$^7$ is hydrogen and the other is C$_1$–C$_4$-alkylcarbonyl, or R$^6$ and R$^7$ together with the nitrogen atom to which they are attached denote a 6-membered heterocyclyl group having one or two nitrogen atoms, or one nitrogen atom and one oxygen atom, in the ring.

6. The pharmaceutical composition of claim 5 in which R$^5$ is an isoquinolinyl group of formula III in which R$^8$ is hydrogen, C$_1$–C$_4$-alkyl, halogen, cyano, —N(R$^6$)R$^7$ where R$^6$ and R$^7$ are independently C$_1$–C$_4$-alkyl or R$^6$ and R$^7$ together with the nitrogen atom to which they are attached denote a 6-membered heterocyclyl group having one or two nitrogen atoms, or one nitrogen atom and one oxygen atom, in the ring, or phenyl substituted by one or two C$_1$–C$_4$-alkoxy groups; R$^9$ and R$^{10}$ are each independently hydrogen, C$_1$–C$_4$-alkyl or halogen; R$^{11}$ and R$^{12}$ are each independently hydrogen, halogen, cyano, carboxy, hydroxy, C$_1$–C$_4$-alkyl, C$_1$–C$_4$-alkoxy or C$_2$–C$_4$-alkynyl, or R$^{11}$ and R$^{12}$ together with the carbon atoms to which they are attached denote a 5-membered heterocycle having two oxygen atoms in the ring; and R$^{13}$ is hydrogen or halogen.

7. The pharmaceutical composition of claim 1 in which R$^1$ is hydrogen or C$_1$–C$_4$-alkyl optionally substituted by hydroxy, C$_1$–C$_4$-alkoxy or C$_1$–C$_4$-alkylthio, R$^2$ is hydrogen, C$_1$–C$_8$-alkyl, hydroxy-C$_1$–C$_8$-alkyl, C$_1$–C$_4$-alkylcarbonyloxy-C$_1$–C$_8$-alkyl, C$_1$–C$_4$-alkoxy-C$_1$–C$_8$-alkyl, C$_1$–C$_4$-alkylthio-C$_1$–C$_8$-alkyl, C$_2$–C$_4$-alkenyl, C$_3$–C$_8$-cycloalkyl-C$_1$–C$_4$-alkyl, heterocyclyl-C$_1$–C$_4$-alkyl where the heterocyclyl group is a 5- or 6-membered heterocyclyl group having one or two hetero atoms selected from nitrogen and oxygen atoms in the ring, phenyl-C$_1$–C$_4$-alkyl in which the phenyl ring is optionally substituted by one or more substituents selected from C$_1$–C$_4$-alkoxy, amino, C$_1$–C$_4$-alkylamino, di(C$_1$–C$_4$-alkyl)amino, C$_1$–C$_4$-alkylcarbonylamino, halogen, C$_1$–C$_4$-alkylsulfonylamino, or di(C$_1$–C$_4$-alkyl)aminosulfonylamino, and is optionally fused to a 5-membered heterocyclic ring having two oxygen or two nitrogen atoms in the ring, R$^3$ is hydrogen or C$_1$–C$_4$-alkyl optionally substituted by hydroxy, C$_1$–C$_4$-alkoxy or C$_1$–C$_4$-alkylthio, R$^4$ is hydrogen or C$_1$–C$_4$-alkyl, R$^5$ is a quinolinyl, isoquinolinyl or oxodihydroisoquinolinyl group optionally fused to a 5-membered heterocyclic group having two oxygen or two nitrogen atoms in the ring and optionally substituted by one or more substituents selected from halogen, cyano, carboxy hydroxy, C$_1$–C$_4$-alkyl, hydroxy-C$_1$–C$_4$-alkyl, C$_1$–C$_4$-alkoxy-C$_1$–C$_4$-alkyl, C$_1$–C$_4$-alkylthio-C$_1$–C$_4$-alkyl, C$_1$–C$_4$-alkoxy, C$_1$–C$_4$-alkylthio, C$_2$–C$_4$-alkenyl, C$_2$–C$_4$-alkynyl, C$_1$–C$_4$-alkylcarbonyl, a group —N(R$^6$)R$^7$ or phenyl optionally substituted by one or more substituents selected from halogen or C$_1$–C$_4$-alkoxy and R$^6$ and R$^7$ are each independently hydrogen or C$_1$–C$_4$-alkyl optionally substituted by hydroxy or alkoxy, or one of R$^6$ and R$^7$ is hydrogen and the other is C$_1$–C$_4$-alkylcarbonyl, or R$^6$ and R$^7$ together with the nitrogen atom to which they are attached denote a 5- or 6-membered heterocyclyl group having one or two nitrogen atoms and, optionally, an oxygen atom in the ring.

8. A pharmaceutical composition comprising a compound of formula

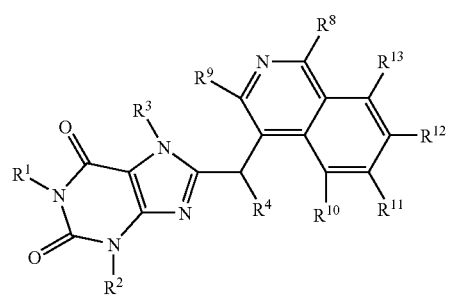

V in free or salt form, wherein
(i) R$^1$ is CH$_3$, R$^2$ is (CH$_3$)$_2$CHCH$_2$, R$^3$ and R$^4$ are each H, R$^8$ is CH$_3$, R$^9$ and R$^{10}$ are each H, and R$^{11}$ and R$^{12}$ are each OCH$_3$; or
(ii) R$^1$ is CH$_3$, R$^2$ is (CH$_3$)$_2$CHCH$_2$, R$^3$, R$^4$, R$^8$, R$^9$ and R$^{10}$ are each H, and R$^{11}$ and R$^{12}$ are each OCH$_3$; or
(iii) R$^1$ is CH$_3$, R$^2$ is (CH$_3$)$_3$CCH$_2$, R$^3$, R$^4$, R$^8$, R$^9$ and R$^{10}$ are each H, and R$^{11}$ and R$^{12}$ are each OCH$_3$; or
(iv) R$^1$ is CH$_3$, R$^2$ is (CH$_3$)$_2$CHCH$_2$, R$^3$, R$^4$, R$^9$ and R$^{10}$ are each H, R$^8$ is Cl and R$^{11}$ and R$^{12}$ are each OCH$_3$; or
(v) R$^1$ is CH$_3$, R$^2$ is (CH$_3$)$_2$CHCH$_2$, R$^3$, R$^4$, R$^8$, R$^9$ and R$^{10}$ are each H, R$^{11}$ is OCH$_3$ and R$^{12}$ is H; or (vi) $R^1$ is $CH_3$, $R^2$ is cyclopropylmethyl, $R^3$, $R^4$, $R^8$, $R^9$, $R^{10}$ and $R^{12}$ are each H and $R^{11}$ is $OCH_3$; or (vii) $R^1$ is $CH_3$, $R^2$ is $(CH_3)_2CHCH_2$, $R^3$, $R^4$, $R^8$, $R^9$, $R^{10}$ and $R^{12}$ are each H and $R^{11}$ is $CH\equiv C$; or (viii) $R^1$ is $CH_3$, $R^2$ is 4-(N-dimethylaminosulfonylamino) benzyl, $R^3$, $R^4$, $R^8$, $R^9$ and $R^{10}$ are each H and $R^{11}$ and $R^{12}$ are each $OCH_3$; or (ix) $R^1$ is $CH_3$, $R^2$ is $HOCH_2CH(CH_3)CH_2$, $R^3$, $R^4$, $R^8$, $R^9$ and $R^{10}$ are each H and $R^{11}$ and $R^{12}$ are each $OCH_3$; or (x) $R^1$ is $CH_3$, $R^2$ is I-methylcyclopropylmethyl, $R^3$, $R^4$, $R^8$, $R^9$ and $R^{10}$ are each H and $R^{11}$ and are each $OCH_3$, and an HMG-CoA reductase inhibitor.

9. The pharmaceutical composition of claim 8 wherein the HMG-CoA reductase inhibitor is simvastatin.

10. A pharmaceutical composition comprising 3-isobutyl-8-(6-methoxy-isoquinolin-4-ylmethyl)-1-methyl-3,7-dihydro-purine-2,6-dione and an HMG-Co-A reductase inhibitor selected from the group consisting of atorvastatin, cerivastatin, fluvastatin, pitavastatin, lovastatin, pravastatin, rosuvastatin and simvastatin.

11. The pharmaceutical composition of claim 10 wherein the HMG-Co-A reductase inhibitor is simvastatin.

\* \* \* \* \*